US005713361A

United States Patent [19]
Ohtomo

[11] Patent Number: 5,713,361
[45] Date of Patent: Feb. 3, 1998

[54] BONE ASSESSMENT APPARATUS

[75] Inventor: Naoki Ohtomo, Mitaka, Japan

[73] Assignee: Aloka Co., Ltd., Tokyo, Japan

[21] Appl. No.: 630,221

[22] Filed: Apr. 10, 1996

[30] Foreign Application Priority Data

Apr. 10, 1995 [JP] Japan .................................. 7-083703

[51] Int. Cl.$^6$ ........................................................ A61B 8/00
[52] U.S. Cl. ........................................................ 128/660.02
[58] Field of Search ........................ 128/660.01, 660.02, 128/661.03; 73/599, 602

[56] References Cited

U.S. PATENT DOCUMENTS

| | | | |
|---|---|---|---|
| 5,335,661 | 8/1994 | Koblauski | 128/661.03 |
| 5,349,959 | 9/1994 | Wiener et al. | 128/661.03 |
| 5,452,722 | 9/1995 | Langtor | 128/661.03 |
| 5,535,750 | 7/1996 | Matsui et al. | 128/661.03 |

FOREIGN PATENT DOCUMENTS

A-0 576 217  12/1883  European Pat. Off. .
A-2 257 253  1/1993  United Kingdom .

*Primary Examiner*—George Manuel
*Attorney, Agent, or Firm*—Fish & Richardson P.C.

[57] ABSTRACT

A bone assessment apparatus includes a pair of ultrasonic transducers (14). A plurality of adapters (26, 126) are available so as to easily adjust the position of the calcaneus in accordance with the size of the foot to be examined. A selected adapter (26, 126) is set on a measuring unit (10). The foot is placed on the selected adapter, and the calcaneus is positioned so as to receive ultrasonic sound beams at its center. The measuring unit (10) includes an adapter identifying section (32), and a control operation unit (30) includes a section (44) for checking whether or not a selected adapter is suitable for the member to be examined.

7 Claims, 6 Drawing Sheets

| PATIENT ID | MEASUREMENT DATE AND TIME | ADAPTER NO. |
|---|---|---|
| | | 1 |
| | | 2 |
| | | 1 |
| | | 3 |
| | | 4 |

BONE ASSESSMENT APPARATUS

BACKGROUND OF THE INVENTION

1. Field of the Invention

The present invention relates to a bone assessment apparatus for diagnosing the physical properties and integrity of a member such as a bone using ultrasound (ultrasonic waves).

2. Description of the Prior Art

Devices for diagnosing bone structures such as a calcaneus using ultrasound are shown and described in International Patent Laid-Open Publication WO93/25,146 and U.S. Pat. No. 3,847,141. In these devices, a pair of ultrasonic transducers are fixedly positioned at opposite sides of a foot supporting plate. The height of the ultrasonic transducers is determined in accordance with a the average height of a calcaneus. The ultrasonic transducers transmit and receive ultrasonic waves therebetween when a foot is in position on the foot supporting plate, thereby monitoring the physical properties and integrity of the calcaneus on the basis of the speed, attenuation and so on of the ultrasonic waves.

X-rays can be used for this purpose so as to diagnose the calcaneus. Japanese Patent Laid-Open Publication Hei 6-22,960 proposes a bone assessment apparatus including a unit for scanning measurement waves.

However, conventional bone assessment apparatuses are usually designed so as to be applicable to an average size adult foot, and the transducers are fixed to a foot supporting plate. Thus, there is a problem when a child's calcaneus is to be examined. The ultrasonic beams (and thus, a measuring point) may diverge from the center of the calcaneus to be examined. In this case, the accuracy of the examination will be reduced.

In order to overcome this problem, it is possible to use a mechanical mechanism to adjust the position of the transducers in accordance with the center of the calcaneus. However, such a mechanism would increase the cost of the bone assessment apparatus. Further, it is troublesome to perform fine control of the transducers for each person to be examined when the apparatus is applied to a group medical examination.

SUMMARY OF THE INVENTION

The present invention is aimed at providing an apparatus which allows a pair of stationary transducers to be adjustable in accordance with a member (e.g. a calcaneus) to be examined of a patient. Further, the present invention is intended to assure reliable and accurate bone assessment.

In order to meet the foregoing objects, there is provided a bone assessment apparatus comprising: a measuring unit; a pair of opposed spaced transducers, one functioning as a transmitter and the other functioning as a receiver, the transducers being positioned on the measuring unit at a predetermined height; and a plurality of adapters for positioning the member to be examined with respect to the measuring waves, the adapters being freely exchangeable and having different shapes.

In this arrangement, one adapter is selected, and is mounted on the measuring unit. The adapter is used to position the member to be examined, with respect to the ultrasonic waves. Thus, the adapters have different sizes and shapes in accordance with the sizes of the members to be examined. When an appropriate adapter is used, the measuring point can be accurately determined for the member to be examined in accordance with the position of the transducers. The transducers are preferably ultrasonic transducers for transmitting and receiving ultrasonic waves. The member to be examined is typically a heel (calcaneus) of a patient.

Each of the adapters includes an adapter base coming in contact with the bottom surface of a foot, and a holder for holding the heel. The holder stands upright from one end of the adapter base. The adapter bases and the holders have different thicknesses.

The adapters have guide marks thereon, which are compared with a reference portion of the member to be examined. An appropriate adapter can be selected using the guide mark. The guide mark is on the upper surface of the adapter base, for example, the position to which the toes of the patient should extend.

The measuring unit preferably includes an adapter identifying section for identifying an adapter which is actually mounted thereon.

Preferably, the measuring unit further includes a database in which identification codes of patients and adapter identification numbers are associated, and a judging unit for comparing results obtained by the adapter identifying section and contents of the database, and checking whether or not an adapter actually mounted on the measuring unit is suitable for the member to be examined.

Other objects, advantages, and features of the invention will become apparent from the following specification when taken in conjunction with the accompanying drawings.

BRIEF DESCRIPTION OF THE DRAWINGS

FIG. 9 shows a database of the bone assessment apparatus.

DESCRIPTION OF THE PREFERRED EMBODIMENTS

Figure 8:
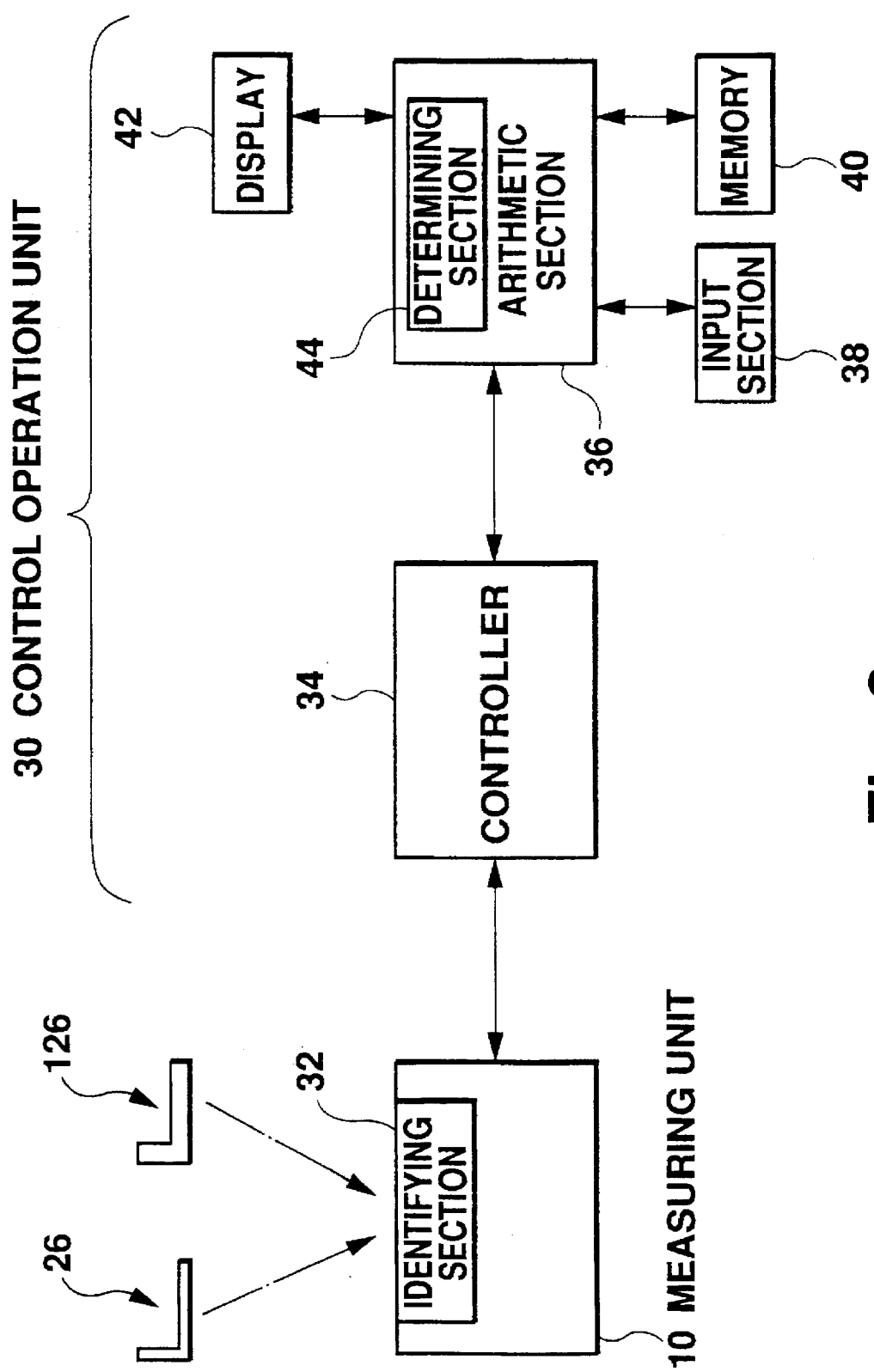
FIG. 8 is a block diagram showing the configuration of the bone assessment apparatus of the invention.

In a preferred embodiment of the invention, a bone assessment apparatus is configured as shown in FIG. 8, and comprises two main parts, a measuring unit 10 and a control operation unit 30.

Figure 1:
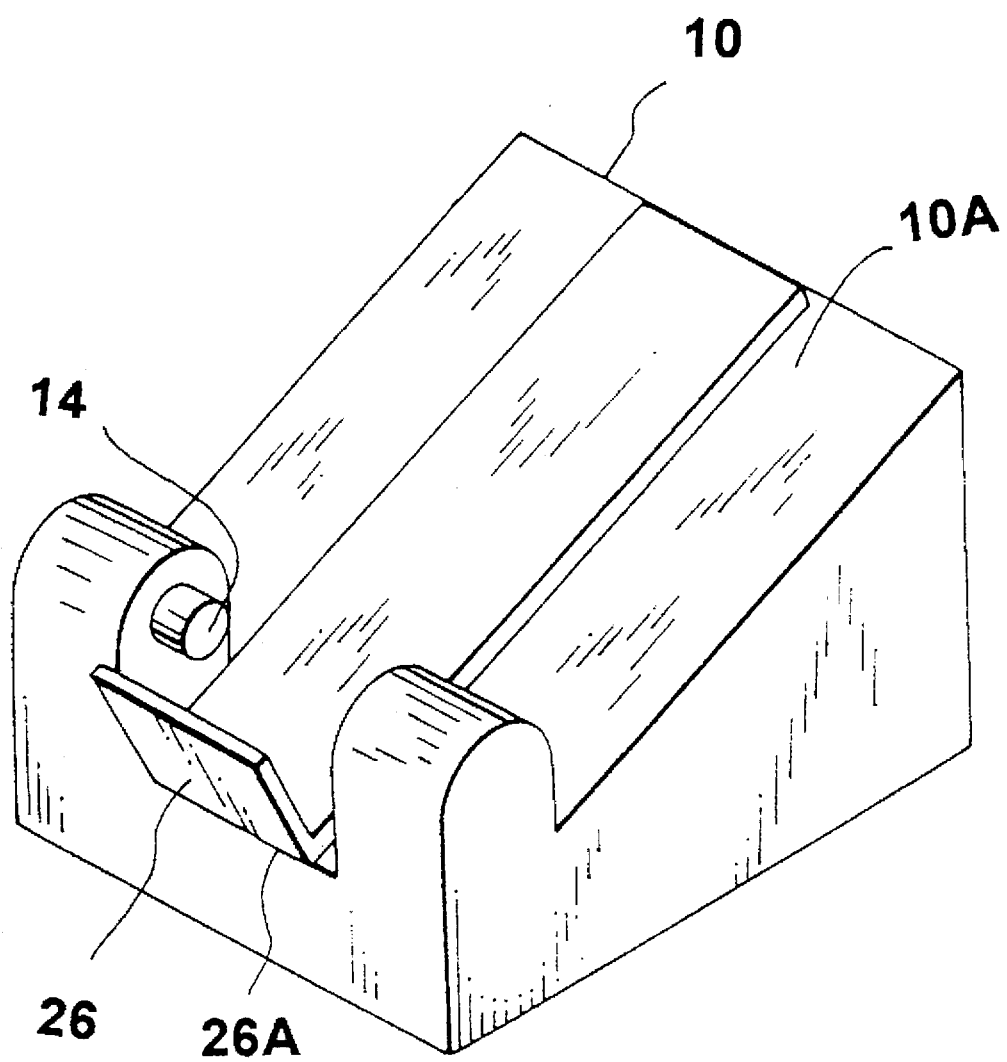
FIG. 1 shows an external view of a measuring unit of a bone assessment apparatus according to the invention.

Referring to FIG. 1, the measuring unit 10 includes a sloped top 10A for receiving an L-shaped adapter 26 thereon. The adapter 26 is detachable from the sloped top 10A. A pair of ultrasonic transducers 14 are opposed and spaced at the side edges of the measuring unit 10, and at a predetermined height therefrom. The ultrasonic transducers 14 transmit and receive ultrasonic waves therebetween. The physical properties, integrity and so on of the calcaneus are analyzed on the basis of the state of the ultrasonic waves after passing through the member to be examined. A space between the two ultrasonic transducers 14 is adjustable using a carrying mechanism (not shown), so the heel is sandwiched between the two ultrasonic transducers 14.

Figure 2:
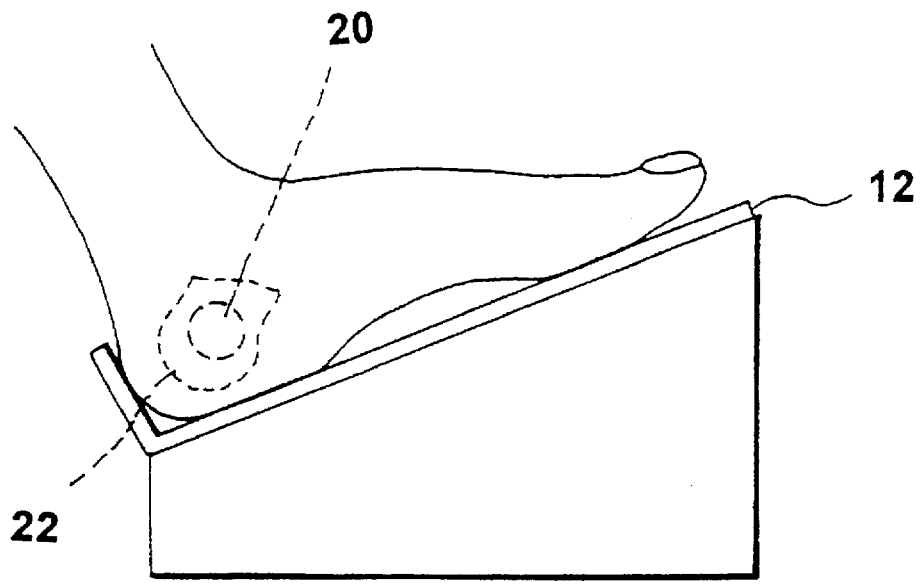
FIG. 2 shows the relationship between ultrasonic transducers and an adults' foot placed on a fixed support plate.
Figure 3:
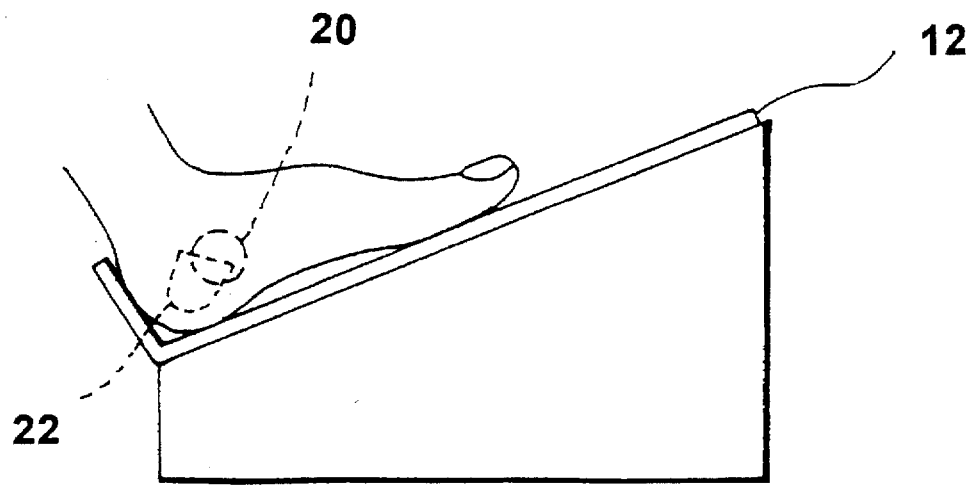
FIG. 3 shows the relationship between the ultrasonic transducers and a child's foot placed on the fixed support plate.

FIGS. 2 and 3 show a comparison between an adult's foot placed on a fixed support plate 12, and a child's foot placed on the same fixed support plate 12. Referring to FIG. 2, a position 20 of the ultrasonic transducers 14 is coincident with the center of the adult's calcaneus. However, the position 20 is quite far from the center of the child's calcaneus, as shown in FIG. 3. In this case, it is impossible to precisely analyze the child's calcaneus.

In order to overcome this problem, the invention includes freely exchangeable adapter 26. An optimum adapter can be selected out of adapters having different sizes in accordance with a size of the member to be examined.

Figure 4:
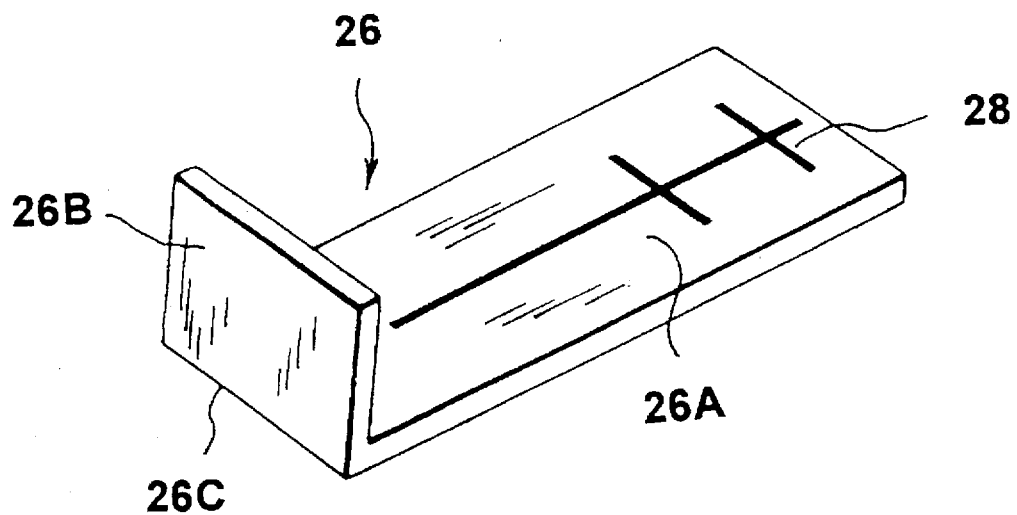
FIG. 4 shows an external view of an adapter for adults.
Figure 5:
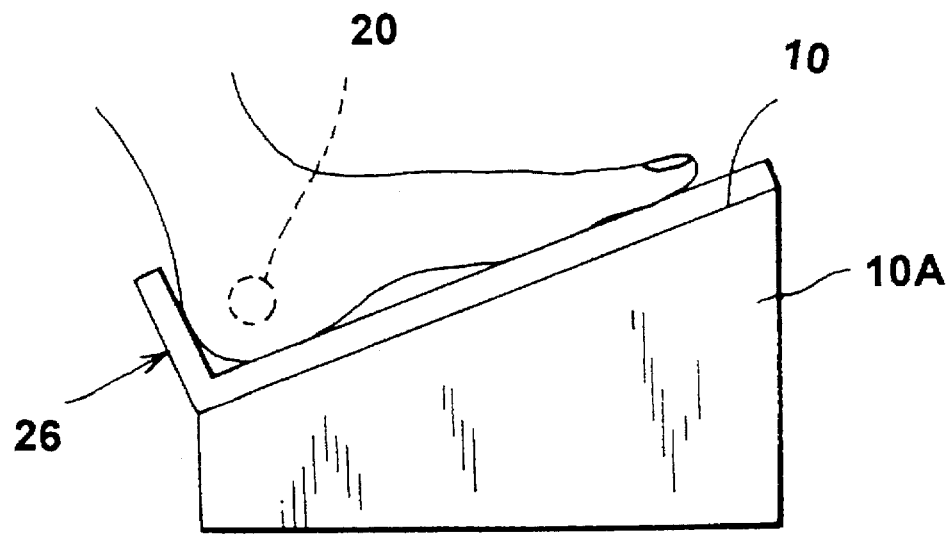
FIG. 5 shows how an adult's foot placed on the adapter of FIG. 4.

The adult's adapter is structured as shown in FIG. 4, and is mounted on the measuring unit 10 as shown in FIG. 5. Similarly, the child's adapter is structured and is mounted on the measuring unit 10 as shown in FIGS. 6 and 7, respectively.

Figure 6:
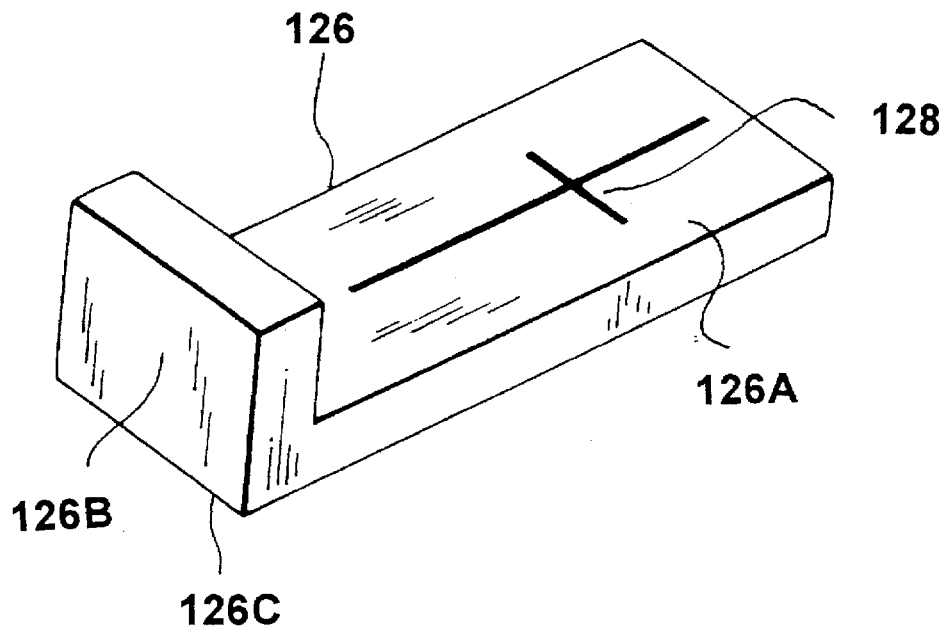
FIG. 6 shows an external appearance of an adapter for the children.
Figure 7:
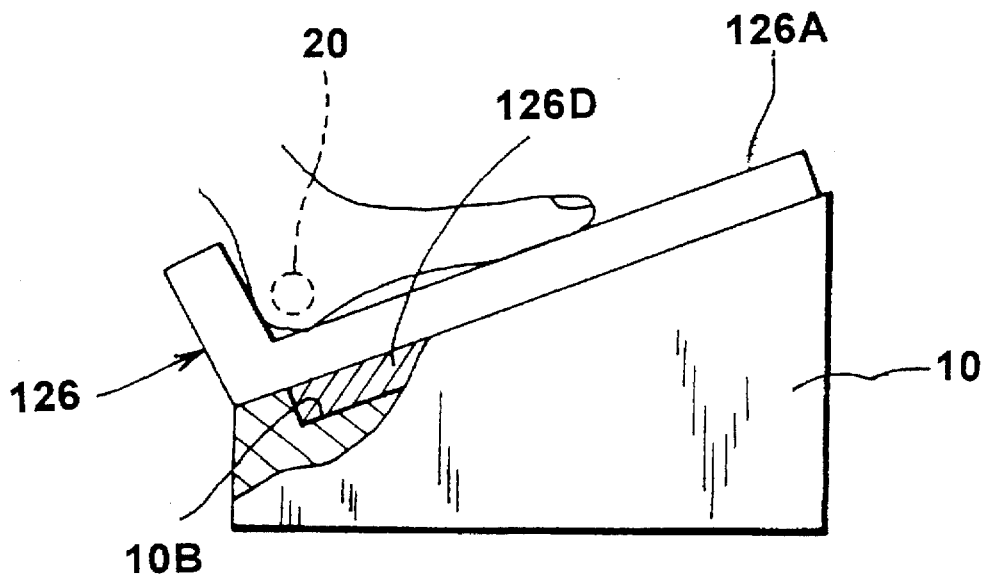
FIG. 7 shows a child's foot placed on the adapter of FIG. 6.

Referring to FIGS. 4 and 6, the adapters 26 and 126 respectively include flat adapter bases 26A and 126A, and heel holders 26B and 126B extending upward from the adapter bases 26A and 126A. The adapters 26 and 126 have an "L" shape. The bottom surface of the foot is placed on the top of the adapter base 26A or 126A, and the rear edge of the foot is in contact with the inner surface of the heel holder 26B or 126B.

As shown in FIG. 1, the top 10A of the measuring unit 10 is sloped in such a manner that the heel is positioned lower than the toes. When the adapter 26 or 126 is placed on the top 10A, a bent portion 26C or 126C is at the lower part of the adapter 26 or 126. When the foot is placed on the adapter 26 or 126, the heel naturally fits into the correct position on the bent portion 26C or 126C.

In the adult's adapter 26, the adapter base 26A and the heel holder 26B are thinner than the adapter base 126A and the heel holder 126B of the child's adapter 126. In other words, the adapters 26 and 126 have different shapes.

The adapter 26 is selected so as to examine adults' heels, while the adapter 126 is selected to examine children's heels (or smaller feet). Thus, it is possible to adjust the position 20 of the ultrasonic transducers with respect to the center of the calcaneus, i.e. the measuring point can be adjusted, without the need of a scanning mechanism for the ultrasonic transducers.

The adults' and children's adapters can be made available in different shapes and sizes, e.g. 5 types of adapters could be prepared. If necessary, adapters for both the left and right foot may be prepared.

Referring to FIG. 7, an under projection 126D is formed under the adapter base 126A, and the measuring unit 10 has a keyway 10B. The projection 126D fits into the keyway 10B. All the adapters 26, 126 have the projections 126D, respectively. This arrangement enables a selected adapter to be easily set on the measuring unit 10.

Guide marks 28 and 128 are placed on the adapter bases 26A and 126A, respectively. Each of the guide marks 28 and 128 includes a longitudinal line and a lateral line intersecting the longitudinal line. The longitudinal line serves as a center line while the lateral line serves as the criteria for selecting an optimum adapter. Specifically, an adapter will be selected such that the toes reach the lateral line when the heel comes into contact with the bent portion 26C. Thus, the selected adapter will be used to determine the center of the calcaneus with respect to the ultrasonic transducers.

FIG. 8 shows the overall configuration of the bone assessment apparatus, which mainly comprises the measuring unit 10 and the control operation unit 30 as described above. The measuring unit 10 receives the adapter thereon. The ultrasonic transducers, and associated transmitter and receiver circuits are not shown in FIG. 8.

In the measuring unit 10, an adapter identifying section 32 identifies a mounted adapter magnetically, optically, electrically or mechanically. For instance, a sensor such as a reed switch or an optical switch may be usable.

The control operation unit 30 includes a controller 34, an arithmetic section 36, an input section 38, a display 42 and a memory 40. The controller 34 controls the operation of the measuring unit 10, and has a transmitter circuit, a receiver circuit, and a control circuit. The arithmetic section 36 calculates values indicative of an analyzed bone, and has a determining section 44. The adapter identifying section 32 provides the arithmetic section 36 with a signal indicative of the identified adapter via the controller 34. The determining section 44 determines whether or not the selected adapter is acceptable for the member to be examined.

The input section 38 is a keyboard or the like, and is used to enter a patient's identification code ID and so on. The memory 40 has a database as shown in FIG. 9. The display 42 indicates various data including a warning if the determining section 44 determines that the selected adapter is not appropriate.

FIG. 9 shows the data base stored in the memory 40. In the data base, a patient identification code, a date and time of measurement, and adapter number are each associated with one another. Specifically, when the adapter code is identified by the adapter identifying section 32, it will be associated with the patient identification code ID.

When a patient is diagnosed for the first time, his or her identification code ID will be stored in the database. At the same time, a date and time of measurement and an adapter number will be automatically stored for the patient. At the time of next assessment, the patient's identification code ID is first entered, and his adapter number will be read by the determining section 44 from the database. The determining section 44 determines whether or not the read adapter number agrees with the adapter number identified by the identifying section 32. If they are not in agreement with each other, a warning will be displayed on the display 42.

Thus, it is possible to prevent erroneous selection of the adapter. Further, since it is possible to automatically check whether or not the same adapter is always used for the same patient, the reliability and accuracy of the measured results can be increased.

As described, the bone assessment apparatus enables an optimum adapter to be selected for a patient in accordance with his foot size, so the ultrasonic waves can accurately pass through the calcaneus.

Further, the guide marks on the adapter facilitate the selection of a suitable adapter.

Still further, it is possible to prevent the selection of an inappropriate adapter on subsequent assessment by using an adapter identifying section.

What is claimed is:

1. A bone assessment apparatus comprising:
   (a) a measuring unit;
   (b) a pair of opposed spaced transducers, one functioning as a transmitter and the other functioning as a receiver, the transducers being positioned on the measuring unit at a predetermined height thereof;

(c) a plurality of adapters for positioning a member to be examined with respect to measuring waves, the adapters being detachable from the measuring unit, freely exchangeable, and having different shapes; and (d) an adapter identifying section provided in the measuring unit for identifying an adapter mounted thereon and for outputting an electrical identification signal indicating the identification result.

2. The apparatus according to claim 1, wherein the transducers are ultrasonic transducers for transmitting and receiving ultrasonic waves.

3. The apparatus according to claim 1, wherein the member to be examined is a heel of a patient.

4. The apparatus according to claim 3, wherein each of the adapters includes an adapter base coming in contact with the bottom surface of a foot, and a holder for holding the heel, the holder standing upright from one end of the adapter base.

5. The apparatus according to claim 4, wherein each of the adapter bases and each of the holders have different thicknesses.

6. The apparatus according to claim 1, further comprising: (d) a database in which identification codes and adapter identification numbers are associated; and (e) a judging unit for comparing the results from the adapter identifying section and contents of the data base, and checking whether or not an adapter actually mounted on the measuring unit is suitable for the member to be tested.

7. A bone assessment apparatus comprising:

(a) a measuring unit;

(b) a pair of opposed spaced transducers, one functioning as a transmitter and the other functioning as receiver, the transducers being positioned on the measuring unit at a predetermined height thereof; and (c) a plurality of adapters for positioning a member to be examined with respect to measuring waves, the adapters being detachable from the measuring unit, freely exchangeable, and having different shades, wherein the adapters comprise guide lines marked thereon for comparing with a reference portion of the member to be examined.

* * * * *